(12) United States Patent  
Coburn

(10) Patent No.: US 7,714,021 B2  
(45) Date of Patent: May 11, 2010

(54) PYRROLIDIN-3-YL COMPOUNDS USEFUL AS BETA-SECRETASE INHIBITORS FOR THE TREATMENT OF ALZHEIMER'S DISEASE

(75) Inventor: Craig A. Coburn, Royersford, PA (US)

(73) Assignee: Merck & Co., Inc., Rahway, NJ (US)

( * ) Notice: Subject to any disclaimer, the term of this patent is extended or adjusted under 35 U.S.C. 154(b) by 671 days.

(21) Appl. No.: 11/629,209

(22) PCT Filed: Jun. 10, 2005

(86) PCT No.: PCT/US2005/020465

§ 371 (c)(1),
(2), (4) Date: Dec. 8, 2006

(87) PCT Pub. No.: WO2006/002004

PCT Pub. Date: Jan. 5, 2006

(65) Prior Publication Data

US 2008/0287523 A1      Nov. 20, 2008

Related U.S. Application Data

(60) Provisional application No. 60/579,794, filed on Jun. 15, 2004.

(51) Int. Cl.
*A61K 31/4025*    (2006.01)
*A61K 31/40*    (2006.01)
*C07D 207/14*    (2006.01)

(52) U.S. Cl. .............. 514/426; 514/422; 548/518; 548/557

(58) Field of Classification Search ............. 548/557; 514/426
See application file for complete search history.

(56) References Cited

U.S. PATENT DOCUMENTS

| 3,577,440 | A * | 5/1971 | Cleveland et al. ........... 548/557 |
| 6,660,741 | B2 | 12/2003 | Bornmann et al. |
| 6,962,934 | B2 | 11/2005 | Warpehoski et al. |
| 7,109,217 | B2 | 9/2006 | Coburn et al. |
| 7,115,652 | B2 | 10/2006 | Yang |
| 7,550,481 | B2 * | 6/2009 | Barrow et al. ............... 514/307 |

| 2004/0132782 | A1 | 7/2004 | Yang et al. |
| 2006/0149092 | A1 | 7/2006 | Nantermet et al. |

FOREIGN PATENT DOCUMENTS

| WO | WO 01/83434 | 11/2001 |
| WO | WO 2005/014540 | 2/2005 |
| WO | WO 2005/016876 | 2/2005 |
| WO | WO 2005/032471 | 4/2005 |
| WO | WO 2005/051914 | 6/2005 |
| WO | WO 2005/065195 | 7/2005 |
| WO | WO 2005/103020 | 11/2005 |
| WO | WO 2005/113484 | 12/2005 |

OTHER PUBLICATIONS

Jordan, V. C. Nature Reviews: Drug Discovery, 2, 2003, pp. 205-213.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
S. G. Pyne et al., "Exo-Diastereoselective 1,3-Dipolar Cycloadditions of Azomethine . . . ", Tetrahedron Letters, vol. 14, pp. 2511-2514 (1995).
S. J. Stachel et al, "Conformationally biased P3 amide replacements of beta-secretase inhibitors", Bioorganic & Medicinal Chemistry Letters, vol. 16, pp. 641-644 (2006).
S. J. Stachel et al., "Structure-based design of Potent and Selective Cell-Permeable Inhibitors of Human beta-secretase (BACE-1)", J. Med. Chem., vol. 47, pp. 6447-6450 (2004).
J. Courcanbeck et al., Design of potential new HIV protease inhibitors: enantioconvergent synthesis of new pyrrolidin-3-ol, and pyrrolidin-3-one peptide conjugates', 2001.
P. Jouin et al., "Stereoselective Synthesis of N-Protected Statine and Its Analogues via Chiral Tetramic Acid", J. Chem. Soc. Perkin Trans., pp. 1177-1182 (1987).

* cited by examiner

*Primary Examiner*—Rebecca L Anderson
*Assistant Examiner*—Matthew P Coughlin
(74) *Attorney, Agent, or Firm*—Keith D. MacMillan; Gerard M. Devlin

(57) ABSTRACT

The present invention is directed to pyrrolidin-3-yl derivative compounds which are inhibitors of the beta-secretase enzyme and that are useful in the treatment of diseases in which the beta-secretase enzyme is involved, such as Alzheimer's disease. The invention is also directed to pharmaceutical compositions comprising these compounds and the use of these compounds and compositions in the treatment of such diseases in which the beta-secretase enzyme is involved.

18 Claims, No Drawings

PYRROLIDIN-3-YL COMPOUNDS USEFUL AS BETA-SECRETASE INHIBITORS FOR THE TREATMENT OF ALZHEIMER'S DISEASE

CROSS-REFERENCE TO RELATED APPLICATIONS

This application claims priority under 35 U.S.C. §119(e) from U.S. provisional application Ser. No. 60/579,794, filed Jun. 15, 2004.

REFERENCE TO JOINT RESEARCH AGREEMENT

This invention was made as a result of activities undertaken within the scope of a Joint Research Agreement between Merck & Co., Inc. and Sunesis Pharmaceuticals, Inc.

BACKGROUND OF THE INVENTION

Alzheimer's disease is characterized by the abnormal deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein (βA4, also referred to as Aβ,β-protein and βAP) which is a proteolytic product of a precursor protein of much larger size. The amyloid precursor protein (APP or AβPP) has a receptor-like structure with a large ectodomain, a membrane spanning region and a short cytoplasmic tail. The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate soluble, COOH-truncated forms of APP ($APP_s$). Proteases that release APP and its fragments from the membrane are termed "secretases." Most $APP_s$ is released by a putative α-secretase which cleaves within the Aβ protein to release α-$APP_s$ and precludes the release of intact Aβ. A minor portion of $APP_s$ is released by a β-secretase ("β-secretase"), which cleaves near the $NH_2$-terminus of APP and produces COOH-terminal fragments (CTFs) which contain the whole Aβ domain.

Thus, the activity of β-secretase or β-site amyloid precursor protein-cleaving enzyme ("BACE") leads to the abnormal cleavage of APP, production of Aβ, and accumulation of β amyloid plaques in the brain, which is characteristic of Alzheimer's disease (see R. N. Rosenberg, Arch. Neurol., vol. 59, September 2002, pp. 1367-1368; H. Fukumoto et al, Arch. Neurol., vol. 59, September 2002, pp. 1381-1389; J. T. Huse et al, J. Biol. Chem., vol 277, No. 18, issue of May 3, 2002, pp. 16278-16284; K. C. Chen and W. J. Howe, Biochem. Biophys. Res. Comm., vol. 292, pp 702-708, 2002). Therefore, therapeutic agents that can inhibit β-secretase or BACE may be useful for the treatment of Alzheimer's disease.

The compounds of the present invention are useful for treating Alzheimer's disease by inhibiting the activity of β-secretase or BACE, thus preventing the formation of insoluble Aβ and arresting the production of Aβ.

SUMMARY OF THE INVENTION

The present invention is directed to novel pyrrolidin-3-yl compounds represented by formula (I)

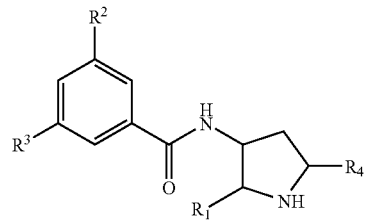

or pharmaceutically acceptable salts thereof, which are useful as inhibitors of the β-secretase enzyme.

The invention is also directed to pharmaceutical compositions which include an effective amount of a compound of formula (I), or pharmaceutically acceptable salts thereof, and a pharmaceutically acceptable carrier. The invention is also directed to methods of treatment of mammals, of diseases in which the β-secretase enzyme is involved, such as Alzheimer's disease, and the use of the compounds and pharmaceutical compositions of the invention in the treatment of such diseases.

DETAILED DESCRIPTION OF THE INVENTION

In one embodiment, the present invention is directed to compounds of formula (I),

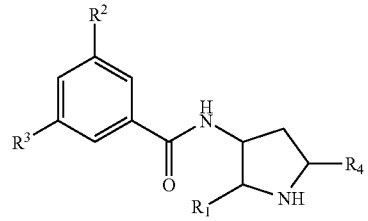

and pharmaceutically acceptable salts thereof, and individual enantiomers and diastereomers thereof, wherein:

$R^1$ is selected from the group consisting of:
(1) hydrogen,
(2) —$C_{1-6}$alkyl,
(3) —$C_{2-6}$alkenyl,
(4) —$C_{2-6}$alkynyl, and
(5) —$(CH_2)_x$-$Q^1$;

$R^2$ is selected from the group consisting of:
(1) ($R^5$—$SO_2$)N($R^7$)—,
(2) $R^5$—S(O)$_m$—,
(3) $R^5$NHC(=O)—,
(4) $R^5$C(=O)NH—,
(5) $R^5R^5N$—,
(6) CN,
(7) —$C_{1-6}$alkyl,
(8) halogen, (9) 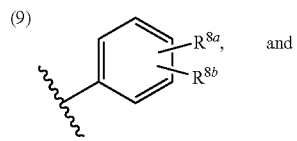 and

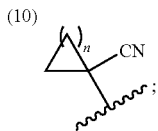

(10)

$R^3$ is selected from the group consisting of:

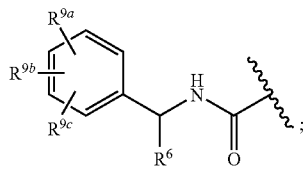

(1)

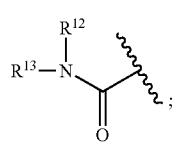

(2)

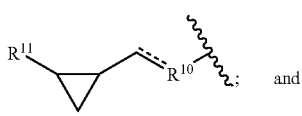

(3) and

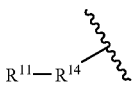

(4)

$R^4$ is selected from the group consisting of:
(1) hydrogen
(2) —$C_{1-6}$alkyl,
(3) —$C_{2-6}$alkenyl,
(4) —$C_{2-6}$alkynyl, and
(5) —$(CH_2)_x$—phenyl;

$R^5$, $R^{5'}$ and $R^6$ are each independently selected from the group consisting of:
(1) —$C_{1-6}$alkyl,
(2) —$C_{2-6}$alkenyl,
(3) —$C_{2-6}$alkynyl,
(4) —$C_{3-8}$ cycloalkyl, and
(5) —$(CH_2)_x$—phenyl;

$R^7$ is selected from the same group as $R^4$;

$R^{8a}$ and $R^{8b}$ are independently selected from the group consisting of:
(1) —CN,
(2) hydrogen,
(3) halogen,
(4) -$Q^2R^5$,
(5) —$C_{1-6}$alkyl,
(6) —$CO_2R^5$, and
(7) tetrazolyl;

$R^{9a}$, $R^{9b}$, $R^{9c}$, $R^{9d}$ and $R^{9e}$ are each independently selected from the group consisting of:
(1) hydrogen,
(2) halogen,
(3) -$Q^2R^5$, and
(4) —$C_{1-6}$alkyl;

$R^{10}$ is selected from the group consisting of
(1) —HC—,
(2) —O—,
(3) —S—, and
(4) —NH—,
provided that when $R^{10}$ is —CH— the dashed line forms a bond and when $R^{10}$ is —O—, —S— or —NH— the dashed line is absent;

$R^{11}$ is selected from the same group as $R^4$;

$R^{12}$ and $R^{13}$ are independently selected from the group consisting of:
(1) —$C_{1-6}$ alkyl;
(2) —$C_{2-6}$ alkyl;
(3) —$C_{2-6}$ alkynyl;
(4) —$(CH_2)_x$—phenyl, or $R^{12}$ and $R^{13}$ are linked together with the nitrogen atom to which they are attached, to form the group

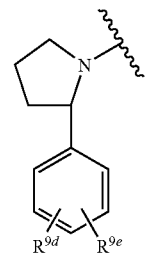

$R^{14}$ is selected from the group consisting of:
(1) —HC═CH—
(2) —O—,
(3) —S—, and
(4) —NH—;

$Q^1$ is selected from the group consisting of
(1) aryl selected from the group consisting of phenyl or naphthyl, and
(2) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl;

$Q^2$ is selected from the group consisting of —O— or —S—;

wherein each $R^1$, $R^2$, $R^4$, $R^5$, $R^{5'}$, $R^6$, $R^7$, $R^{8a}$, $R^{8b}$, $R^{9a-9e}$, $R^{11}$, $R^{12}$ and $R^{13}$ alkyl, alkenyl and alkynyl moiety group herein is unsubstituted or substituted with one or more
(a) halo,
(b) —OH,
(c) —CN,
(d) —$C_{1-10}$ alkyl
(e) —$C_{3-8}$ cycloalkyl,
(f) —O—$C_{1-10}$ alkyl,
(g) aryl selected from the group consisting of phenyl or naphthyl,
(h) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl, and (i) —$NR^7R^{11}$;

and each $R^4$, $R^5$, $R^{5'}$, $R^6$, $R^7$, $R^{11}$, $R^{12}$, $R^{13}$ and $Q^1$ phenyl or naphthyl moiety herein is unsubstituted or substituted with one or more (a) halo, (b) —OH, (c) —CN, (d) —$C_{1-10}$alkyl (e) —$C_{3-8}$ cycloalkyl, (f) —O—$C_{1-10}$ alkyl, (g) aryl selected from the group consisting of phenyl or naphthyl, (h) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl, and (i) —$NR^7R^{11}$;

m is independently 0, 1, or 2; and x is independently 0 or 1.

Within this embodiment, there is a sub-genus of compounds and pharmaceutically acceptable salts thereof wherein:

$R^1$ is —(CH$_2$)-phenyl or phenyl, wherein the phenyl moiety is optionally substituted, and preferably wherein the phenyl moiety is substituted with one halogen, preferably chloro or fluoro;

$R^4$ is hydrogen or $C_{1-6}$ alkyl, preferably hydrogen; and $R^2$ is selected from the group consisting of:

(1) ($R^5$—SO$_2$)N($R^7$)—, wherein $R^5$ and $R^7$ are preferably $C_{1-6}$ alkyl,

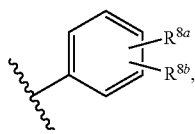

(2)

wherein $R^{8a}$ is preferably hydrogen and $R^{8b}$ is preferably cyano or halogen, and

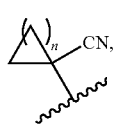

(3)

wherein n is preferably 3.

In another embodiment, the invention is directed to compounds of formula (II), and pharmaceutically acceptable salts thereof, and individual enantiomers and diastereomers thereof, wherein:

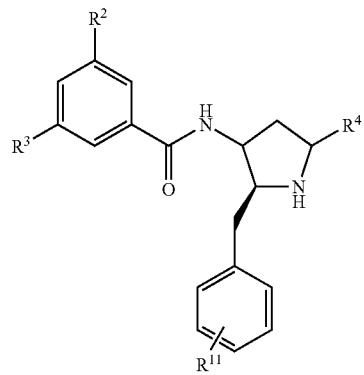

(II)

wherein $R^2$, $R^3$ and $R^4$ are as defined above, and $R^{11}$ is selected from the group consisting of (1) halo, (2) —OH, (3) —CN, and (4) —O—$C_{1-10}$ alkyl.

Within this embodiment, there is a sub-genus of compounds and pharmaceutically acceptable salts thereof wherein:

$R^{11}$ is halogen, preferably chloro or fluoro;

$R^2$ is selected from the group consisting of:

(1) ($R^5$—SO$_2$)N($R^7$)—, wherein $R^5$ and $R^7$ are preferably $C_{1-6}$ alkyl,

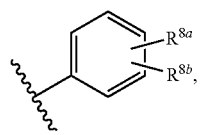

(2)

wherein $R^{8a}$ is preferably hydrogen and $R^{8b}$ is preferably cyano or halogen, and

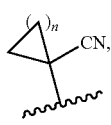

(3)

wherein n is preferably 3; and $R^4$ is hydrogen or $C_{1-6}$ alkyl, preferably hydrogen.

In another embodiment, the invention is directed to compounds of formula (III), and pharmaceutically acceptable salts thereof, and individual enantiomers and diastereomers thereof, wherein:

(III)

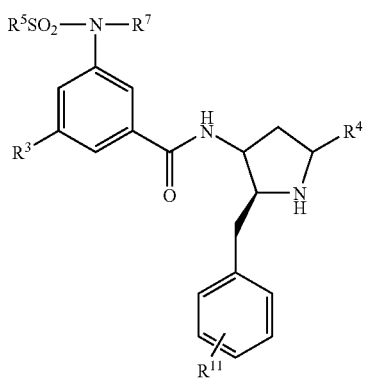

wherein $R^3$, $R^4$, $R^5$ and $R^7$ are as defined above, and $R^{11}$ is selected from the group consisting of
(1) halo,
(2) —OH,
(3) —CN, and
(4) —O—$C_{1-10}$ alkyl.

Within this embodiment, there is a sub-genus of compounds and pharmaceutically acceptable salts thereof wherein:
$R^5$ and $R^7$ are each $C_{1-6}$ alkyl; and
$R^4$ is hydrogen or $C_{1-6}$ alkyl, preferably hydrogen.

In another embodiment, the invention is directed to compounds of formula (IV)

(IV)

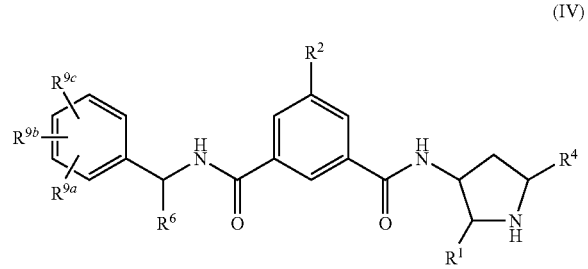

wherein $R^1$, $R^2$, $R^4$, $R^6$, $R^{9a}$, $R^{9b}$ and $R^{9c}$ are as defined above.

Within this embodiment, there is a sub-genus of compounds and pharmaceutically acceptable salts thereof wherein:
$R^4$ is $C_{1-6}$ alkyl, and $R^{9a}$ and $R^{9c}$ are hydrogen and $R^{9b}$ is halogen, preferably chloro or bromo;
$R^1$ is —(CH$_2$)-phenyl or phenyl, wherein the phenyl moiety is optionally substituted, and preferably the phenyl moiety is substituted with one halogen, for example chloro or fluoro;
$R^2$ is selected from the group consisting of:
(1) ($R^5$—SO$_2$)N($R^7$)—, wherein $R^5$ and $R^7$ are preferably $C_{1-6}$ alkyl, (2)

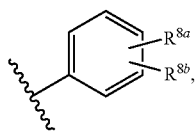

wherein $R^{8a}$ is preferably hydrogen and $R^{8b}$ is preferably cyano or halogen, and (3)

wherein n is preferably 3; and
$R^4$ is hydrogen or $C_{1-6}$ alkyl, preferably hydrogen.

In other embodiments, the invention is directed to compounds of formula (V), and pharmaceutically acceptable salts thereof, and individual enantiomers and diastereomers thereof, wherein:

(V)

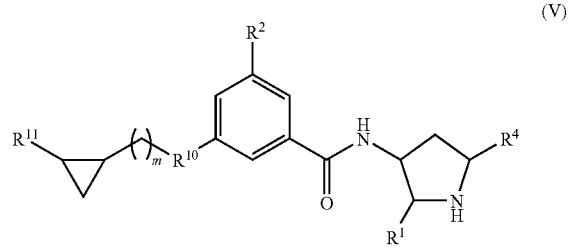

wherein $R^1$, $R^2$, $R^4$, $R^{10}$, $R^{11}$ and m are as defined above.

Within this embodiment, there is a sub-genus of compounds and pharmaceutically acceptable salts thereof wherein:
$R^{11}$ is $C_{1-6}$ alkyl or phenyl;
$R^1$ is —(CH$_2$)-phenyl or phenyl, wherein the phenyl moiety is optionally substituted, and preferably the phenyl moiety is substituted with one halogen, preferably chloro or fluoro;
$R^2$ is selected from the group consisting of:
(1) ($R^5$—SO$_2$)N($R^7$)—, wherein $R^5$ and $R^7$ are preferably $C_{1-6}$ alkyl, (2)

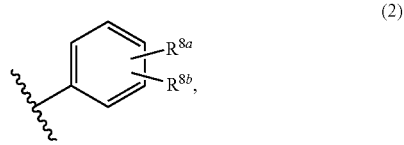

wherein $R^{8a}$ is preferably hydrogen and $R^{8b}$ is preferably cyano or halogen, and (3)

wherein n is preferably 3; and
$R^4$ is hydrogen or $C_{1-6}$ alkyl, preferably hydrogen.

In another embodiment, the invention is directed to compounds of formula (VI), and pharmaceutically acceptable salts thereof, and individual enantiomers and diastereomers thereof, wherein:

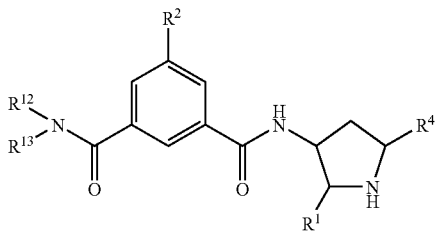

(VI)

wherein $R^1$, $R^2$, $R^4$, $R^{12}$ and $R^{13}$ are as defined above.

Within this embodiment, there is a sub-genus of compounds and pharmaceutically acceptable salts thereof, wherein:

$R^{12}$ and $R^{13}$ are each $C_{1-6}$ alkyl, or $R^{12}$ and $R^{13}$ are linked together with the nitrogen atom to which they are attached to form a pyrrolidinyl ring, as depicted in formula (VII):

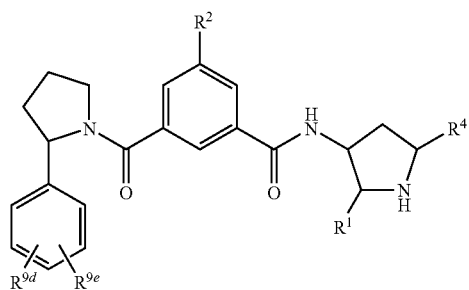

(VII)

wherein $R^1$, $R^2$, $R^4$, $R^{9d}$ and $R^{9e}$ are as defined above;

$R^1$ is —(CH$_2$)-phenyl or phenyl, wherein the phenyl moiety is optionally substituted, and preferably the phenyl moiety is substituted with one halogen, for example chloro or fluoro;

$R^2$ is selected from the group consisting of:

(1) $(R^5$—SO$_2)$N$(R^7)$—, wherein $R^5$ and $R^7$ are preferably $C_{1-6}$ alkyl,

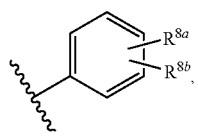

(2)

wherein $R^{8a}$ is preferably hydrogen and $R^{8b}$ is preferably cyano or halogen, and

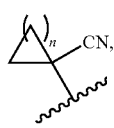

(3)

wherein n is preferably 3; and $R^4$ is hydrogen or $C_{1-6}$ alkyl, preferably hydrogen.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six carbon atoms. Exemplary alkyl groups include methyl, ethyl, n-propyl, isopropyl, n-butyl, isobutyl, tert-butyl, pentyl, hexyl, and the like.

As used herein, the term "alkoxy," by itself or as part of another substituent, means the group —O— alkyl, wherein alkyl is defined above, having the number of carbon atoms designated (e.g., $C_{1-10}$ alkoxy means an alkoxy group having from one to ten carbon atoms. Preferred alkoxy groups for use in the invention are $C_{1-6}$ alkoxy groups, having from one to six carbon atoms. Exemplary preferred alkoxy groups include methoxy, ethoxy, propoxy, butoxy, sec-butoxy and pentoxy. Especially preferred alkoxy groups are $C_{1-3}$ alkoxy.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, the term "alkynyl," by itself or as part of another substituent, means a straight or branched chain hydrocarbon radical having a single carbon-carbon triple bond and the number of carbon atoms designated (e.g., $C_{2-10}$ alkynyl means an alkynyl group having from two to ten carbon atoms). Preferred alkynyl groups for use in the invention are $C_{2-6}$ alkynyl groups, having from two to six carbon atoms. Exemplary alkynyl groups include ethynyl and propynyl.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, as well as bridged and fused ring carbocycles, such as spiro fused ring systems.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantly and norbornyl. Exemplary fused cycloalkyl groups include decahydronaphthalene.

As used herein, the term "aryl," by itself or as part of another substituent, means an aromatic or cyclic radical having the number of carbon atoms designated (e.g., $C_{6-10}$ aryl means an aryl group having from six to ten carbons atoms). The term "aryl" includes multiple ring systems as well as single ring systems. Preferred aryl groups for use in the invention include phenyl and naphthyl.

The term "halo" or "halogen" includes fluoro, chloro, bromo and iodo.

As used herein, the term "heteroaryl," by itself or as part of another substituent, means an aromatic cyclic group having at least one ring heteroatom (O, N or S). The term "heteroaryl" includes multiple ring systems as well as single ring systems. Exemplary heteroaryl groups for use in the invention include furyl, pyranyl, benzofuranyl, isobenzofuranyl, chromenyl, thienyl, benzothiophenyl, pyrrolyl, pyrazolyl, imidazolyl, pyridyl, pyrazinyl, pyrimidinyl, pyridazinyl, indolyl, indazolyl, benzimidazolyl, quinolyl, tetrazolyl and isoquinolyl.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. When a heteroaryl group is defined as a substituent herein, the point of attachment may be at a ring carbon atom of the heteroaryl group, or on a ring heteroatom (i.e., a nitrogen, oxygen or sulfur) which has a valence which permits attachment. Preferably, the attachment is at a ring carbon atom.

Some of the compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

Compounds described herein may contain one or more double bonds, and may thus give rise to cis/trans isomers as well as other conformational isomers. The present invention includes all such possible isomers as well as mixtures of such isomers.

Formulas (I) to (VII) are shown above without a definite stereochemistry at certain positions. The present invention includes all stereoisomers of Formulas (I) to (VII) and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer of a compound may be obtained by stereoselective synthesis using optically pure starting materials or reagents of known configuration by methods well known in the art.

The compounds claimed in this invention can be prepared according to the following general procedure methods, and the specific examples.

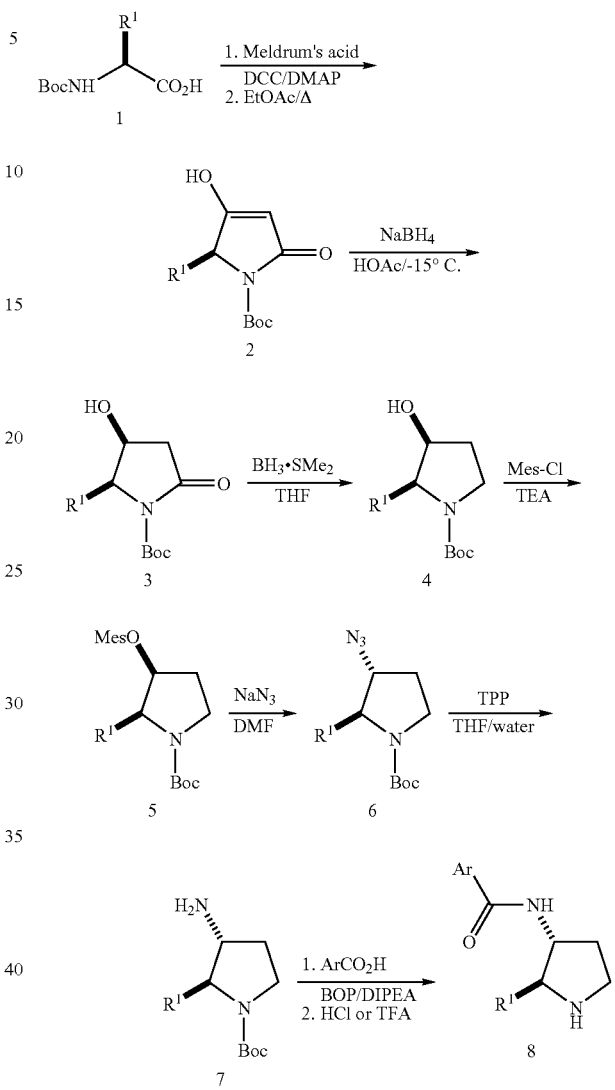

An appropriately protected amino acid 1 can be condensed with Meldrum's acid using a coupling agent such as DCC and DMAP to afford an intermediate which can be rearranged to the tetramic acid derivative 2 upon heating in a solvent such as ethyl acetate. Reduction of 2 can be accomplished at low temperature, preferably −5° to −15° C., by reaction with a hydride source such as $NaBH_4$ in acetic acid to give compounds 3, that can be further reduced to pyrrolidines 4 with borane in THF. The hydroxyl group can be activated for displacement by conversion to the corresponding mesylate ester 5 using mesyl chloride and a tertiary amine. Displacement of the mesylate group can be achieved by subjecting intermediate 5 to an excess of azide salt in a polar aprotic solvent such as DMF at elevated temperatures, to form 6. The azido group of 6 can be reduced to the amine using any of a number of known methods, such as hydrogenation or a Staudinger reaction, to form 7. Amino pyrrolidine 7 can then be coupled to a benzoic acid derivative using a BOP mediated protocol to give the penultimate compounds 8, which can then be deprotected using a strong acid such as TFA in DCM or HCl gas.

General scheme B

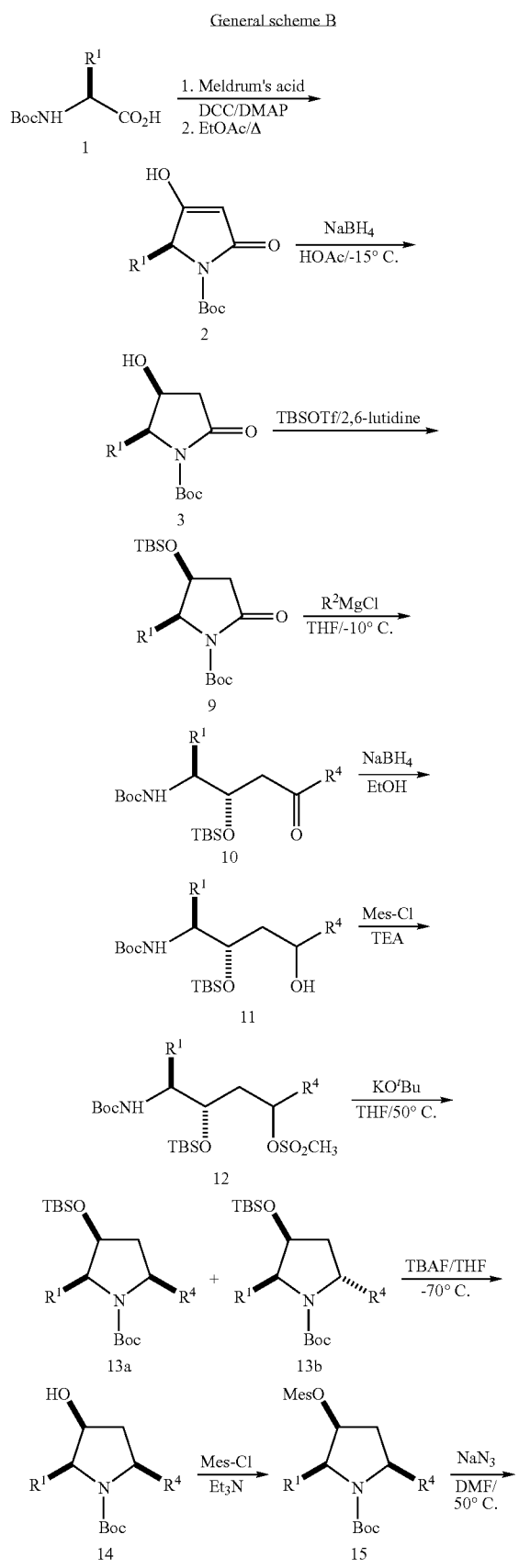

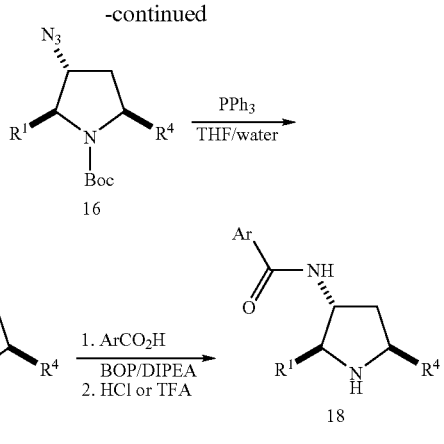

Scheme B can be used as an extension of scheme A to allow for the incorporation of groups at C-5 of the pyrrolidine ring. As such, intermediate 3 can be protected as its TBS ether by standard protocol and ketone 10 can be produced by reaction of 9 with an appropriately substituted Grignard reagent. Ketone 10 can be reduced, activated and cyclized using conditions outlined in the scheme to afford mixtures of cis and trans pyrrolidines 13. Separation of the isomers give pure 13 which can be deprotected with a fluoride source such as TBAF and the resulting alcohol 14 carried forth in a manner similar to that outlined in scheme A to afford inhibitors 18.

The term "substantially pure" means that the isolated material is at least 90% pure, and preferably 95% pure, and even more preferably 99% pure as assayed by analytical techniques known in the art.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, trifluoroacetic, maleic, phosphoric, sulfuric, fumaric, and tartaric acids.

The present invention is directed to the use of the compounds of formulas (I) to (VII) disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangeably in this specification. In addition to humans, a variety of other mammals can be treated according to the method of the present invention.

The present invention is further directed to a method for the manufacture of a medicament or a composition for inhibiting β-secretase enzyme activity in humans and animals comprising combining a compound of the present invention with a pharmaceutical carrier or diluent.

The compounds of the present invention have utility in treating, ameliorating, controlling or reducing the risk of Alzheimer's disease. For example, the compounds may be useful for the prevention of dementia of the Alzheimer's type, as well as for the treatment of early stage, intermediate stage or late stage dementia of the Alzheimer's type. The compounds may also be useful in treating, ameliorating, controlling or reducing the risk of diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, Down syndrome, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with anti-Alzheimer's agents, for example other beta-secretase inhibitors or gamma-secretase inhibitors; tau phosphorylation inhibitors; blockers of Aβ oligomer formation; p25/CDK5 inhibitors; NK1/NK3 receptor antagonists; HMG-CoA reductase inhibitors; NSAIDs including ibuprofen; vitamin E; anti-amyloid antibodies, including anti-amyloid humanized monoclonal antibodies; CB-1 receptor antagonists or CB-1 receptor inverse agonists; anti-inflammatory compounds such as (R)-flurbiprofen; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine $H_3$ antagonists; AMPA agonists; PDE IV inhibitors; $GABA_A$ inverse agonists; neuronal nicotinic agonists; P-450 inhibitors, such as ritonavir; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound, which is a compound of formulas (I) to (VII), is included in an amount sufficient to produce the desired effect upon the process or condition of diseases. Accordingly, the pharmaceutical compositions of the present invention encompass any composition made by admixing a compound of the present invention and a pharmaceutically acceptable carrier.

The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds represented by Formulas (I) to (VII), or pharmaceutically acceptable salts thereof, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can also be in a form suitable for rectal administration wherein the carrier is a solid. It is preferable that the mixture forms unit dose suppositories. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician. As used herein, the term "treatment" refers to the treatment of the mentioned conditions, particularly in a patient who demonstrates symptoms of the disease or disorder.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology). The term "controlling" includes preventing treating, eradicating, ameliorating or otherwise reducing the severity of the condition being controlled.

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating, ameliorating, controlling or reducing the risk of Alzheimer's disease or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The amount of active ingredient that may be combined with the carrier materials to produce a single dosage form will vary depending upon the host treated and the particular mode of administration. For example, a formulation intended for the oral administration to humans may conveniently contain from about 0.005 mg to about 2.5 g of active agent, compounded with an appropriate and convenient amount of carrier material. Unit dosage forms will generally contain between from about 0.005 mg to about 1000 mg of the active ingredient, typically 0.005 mg, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of β-secretase enzyme activity may be demonstrated by methodology known in the art. Enzyme inhibition is determined as follows.

ECL Assay: A homogeneous end point electrochemiluminescence (ECL) assay is employed using a biotinylated BACE substrate. The Km of the substrate is greater than 100 μM and can not be determined due to the limit of solubility of the substrate. A typical reaction contains approximately 0.1 nM enzyme, 0.25 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction proceeds for 30 min and is then stopped by the addition of 25 μL of 1 M Tris-HCl, pH 8.0. The resulting enzymatic product is assayed by adding a ruthenylated antibody which specifically recognizes the C-terminal residue of the product. Streptavidin coated magnetic beads are added into the solution and the samples are subjected to M-384 (Igen Inc., Gaithersburg, Md.) analysis. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, 12 concentrations of inhibitors are prepared starting from 100 μM with three fold series dilution. Solutions of the inhibitor in DMSO are included in the reaction mixture (final DMSO concentration is 10%). All experiments are conducted at rt using the standard reaction conditions described above. To determine the $IC_{50}$ of the compound, a four parameter equation is used for curve fitting. The errors in reproducing the dissociation constants are typically less than two-fold.

HPLC assay: A homogeneous end point HPLC assay is used with the substrate (coumarin-CO-REVNFEVEFR), which is cleaved by BACE 1 to release the N-terminal fragment attached with coumarin. The Km of the substrate is greater than 100 μM and can not be determined due to the limit of solubility of the substrate. A typical reaction contains approximately 2 μM enzyme, 1.0 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction is proceeded for 30 min and the reaction is stopped by the addition of 25 μL of 1 M Tris-HCl, pH 8.0. The resulting reaction mixture is loaded on the HPLC and the product is separated from substrate with 5 min linear gradient. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, 12 concentrations of inhibitors are prepared, and the concentration rage is dependent on the potency predicted by ECL. Solutions of inhibitor in DMSO are included in the reaction mixture (final DMSO concentration is 10%). All experiments are conducted at rt using the standard reaction conditions described above. To determine the $IC_{50}$ of the compound, four parameters equation is employed for curve fitting. The errors in reproducing the dissociation constants are typically less than two-fold.

In particular, the compounds of the following examples had activity in inhibiting the beta-secretase enzyme in the aforementioned assays, generally with an $IC_{50}$ from about 1 nM to 100 μM. Such a result is indicative of the intrinsic activity of the compounds in use as inhibitors of beta-secretase enzyme activity.

Several methods for preparing the compounds of this invention are illustrated in the schemes and examples herein. Starting materials are made according to procedures known in the art or as illustrated herein. The following examples are provided so that the invention might be more fully understood. These examples are illustrative only and should not be construed as limiting the invention in any way.

The following abbreviations are used throughout the text:
Me: methyl
Et: ethyl
t-Bu: tert-butyl
Ar: aryl
Ac: acetyl
THF: tetrahydrofuran
DMSO: dimethylsulfoxide
EDTA: ethylene diamine tetraacetic acid
Boc: tert-butyloxy carbonyl
BOP: Benzotriazol-1-yloxy-tris(dimethylamino)phosphonium hexafluorophosphate
CHAPS: 3-[(3-cholamidopropyl)dimethylammonio]-2-hydroxy-1-propanesulfonate
DIPEA: diisopropylethylamine
DCM: dichloromethane
BSA: bovine serum albumin
Tf: tri-fluoromethylsulfonyl
TFA: trifluoracetic acid
DMAP: 4-dimethylaminopyridine
DCC: dicyclohexylcarbodiimide
TEA: triethylamine
Mes: methanesulfonyl
DMF: N,N-dimethylformamide
TPP: triphenyl phosphine
TBS: tert-butyl dimethyl-silyl
TBSOTf: tert-butyldimethylsilyl triflate Phe: phenylalanine
TBAF: tetra-n-butylammonium fluoride
NIS: N-iodo succinimide
PCC: pyridinium chlorochromate
DIBAL: diisobutylaluminum hydride
DMI: 1,3-dimethyl-2-imidazolidinone
rt: room temperature
HPLC: high performance liquid chromatography Intermediate I: (Route A)
(2S,3R)-2-benzyl-1-methylpyrrolidin-3-amine

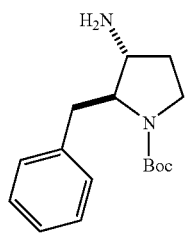

Step A: To a 0° C. solution of N-Boc-L-Phe (1.99 g, 7.54 mmol), Meldrum's acid (1.2 g, 8.29 mmol) and DMAP (1.38 g, 11.31 mmol) in 20 mL of DCM was added a 1M solution of DCC in DCM (9.05 mL, 9.05 mmol) by dropping funnel over 15 min. The resulting mixture was allowed to stir to rt over 4 hours. The slurry was cooled to 0° C. and diluted with 125 mL of EtOAc and filtered. The filtrate was washed with cold 10% citric acid (2×25 mL), water (2×25 mL), and brine (25 mL). The organic layer was dried over MgSO4 and concentrated to leave the desired material that was used without further purification. LCMS (M+H)=392.21.

Step B: Nitrogen gas was passed through a stirred solution of compound 1-A (2.95 g, 7.54 mmol) in 20 mL of EtOAc while the reaction was heated at reflux for 20 min. The solution was cooled, concentrated and the precipitate was collected to leave the desired tetramic acid derivative 1-B. $^1$H NMR (DMSO d6) δ 7.07 (m, 3H), 6.77 (m, 2H), 4.49 (s, 1H), 4.41 (bd, 1H), 3.15 (dd, J=13.8, 5.1 Hz, 1H), 2.94 (m, 1H), 1.29 (s, 9H). LCMS (M-tBu)=234.15

Step C: To a −15° C. solution containing 1-B (1.08 g, 3.73 mmol) in 20 mL of DCM was added 3.4 mL (60 mmol) of HOAc followed the portion-wise addition of 565 mg (14.9 mmol) of NaBH$_4$. The resulting solution was stirred to −5° C. over 5 h and quenched with 50 mL of 10% citric acid. The aqueous phase was separated and extracted with CH$_2$Cl$_2$ (3×25 mL). The combined organic extracts were washed with water (2×25 mL) then brine (25 mL) and dried over MgSO$_4$. Column chromatography (4:1 EtOAc/Hexanes) left the desired lactam as a white solid. $^1$H NMR (CDCl$_3$) δ 7.27-7.05 (m, 5H), 4.59-4.39 (m, 2H), 3.21-3.05 (m, 2H), 2.66 (dd, J=13.5, 4.8 Hz, 1H), 2.44 (dd, J=16.7, 6.8 Hz, 1H), 1.78 (m, 1H), 1.39 (s, 9H). LCMS (M-$^t$Bu)=236.16

Step D: A solution of 10 M borane dimethylsulfide (0.82 mL, 8.2 mmol) was added to a rt solution of the lactam from step C (840 mg, 2.88 mmol) in 20 mL of THF and the resulting mixture was heated at reflux for 45 min. The reaction was cooled and poured into 100 mL of ether and the excess borane was quenched by the slow addition of saturated NH$_4$Cl. The two phases were separated and the organic was washed with 10% citric acid (2×15 mL), water and brine. Column chromatography (gradient: 1:1 EtOAc/Hexanes to EtOAc) left the desired pyrrolidine. $^1$H NMR (CDCl$_3$) δ 7.25-7.09 (m, 5H), 4.29 (dd, 1H), 4.04 (bs, 1H), 3.48-3.33 (m, 2H), 3.01 (dd, 1H), 2.85 (dd, 1H), 1.78 (m, 2H), 1.36 (s, 9H). LCMS (M-$^t$Bu)= 222.19

Step E: To a 0° C. solution containing 310 mg (1.12 mmol) of the alcohol from step D in 5 mL of DCM was added 0.156 mL (1.12 mmol) of TEA and 0.087 mL (1.12 mmol) of methanesulfonyl chloride. The reaction mixture was stirred for 1 h, diluted with 25 mL of DCM and extracted with water then brine. The organic phase was dried over MgSO$_4$ and concentrated to leave an oily residue that was used directly in the next reaction without further purification. LCMS (M-$^t$Bu)=300.17

Step F: A solution containing 397 mg (1.12 mmol) of the mesylate from step E and sodium azide (726 mg, 11.2 mmol) in 3 mL of DMF was heated at 55° C. for 17 h. The reaction mixture was diluted with 50 mL of EtOAc and extracted with 7×5 mL of water then 10 mL of brine. Column chromatography (5% to 50% EtOAc/Hexanes) provided the desired azide. LCMS (M-$^t$Bu)=247.20.

Step G: Triphenylphoshine (239 mg, 0.91 mmol) was added to a solution of azide 1-F (230 mg, 0.76 mmol) in 3 mL of THF containing 0.02 mL of water and the resulting reaction mixture was heated at 45° C. for 17 h. The reaction mixture was cooled and concentrated and the residue was purified by column chromatography (9:1 EtOAc/EtOH) to provide intermediate I as a white solid. LCMS (M-$^t$Bu)=221.20.

Intermediate II: (2S,3R)-2-(2-chlorobenzyl)-1-methylpyrrolidin-3-amine

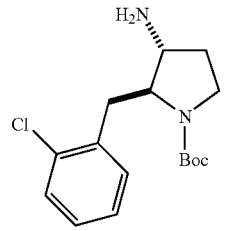

This compound was prepared in a similar manner to intermediate I but substituting (S)-N-Boc-2-chlorophenylalanine in place of Boc-L-Phe as the reactant. $^1$H NMR (CDCl$_3$) δ 7.35 (m, 1H), 7.19 (m, 3H), 4.39-4.31 (m, 1H), 3.66 (m, 2H), 3.45 (m, 1H), 3.03-2.97 (m, 2H), 2.22-2.13 (m, 2H), 1.37 (s, 9H). LCMS (M-$^t$Bu)=255.19

Intermediate III: (2S,3R)-2-(3-chlorobenzyl)-1-methylpyrrolidin-3-amine

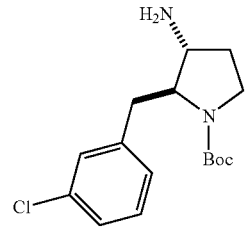

This compound was prepared in a similar manner to intermediate I but substituting (S)-N-Boc-3-chlorophenylalanine in place of Boc-L-Phe as the reactant. $^1$H NMR (CDCl$_3$)

δ 8.28 (bs, 2H), 7.22 (m, 2H), 7.12 (s, 1H), 7.02 (m, 1H), 4.28-4.15 (m, 1H), 3.55 (m, 2H), 3.31 (m, 1H), 2.88 (m, 1H), 2.75 (m, 1H), 1.88 (m, 2H), 1.39 (s, 9H). LCMS (M−'Bu)= 255.19

Intermediate IV: (2S,3R)-2-(4-chlorobenzyl)-1-methylpyrrolidin-3-amine

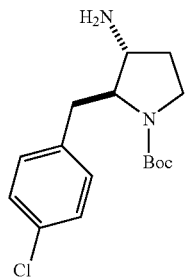

This compound was prepared in a similar manner to intermediate I but substituting (S)-N-Boc-4-chlorophenylalanine in place of Boc-L-Phe as the reactant. ¹H NMR (CDCl₃) δ 8.58 (bs, 2H), 7.27 (m, 2H), 7.12 (m, 2H), 4.21-4.13 (m, 1H), 3.55 (m, 2H), 3.28 (m, 1H), 2.96 (m, 1H), 2.59 (m, 1H), 2.03-1.92 (m, 2H), 1.46 (s, 9H). LCMS (M−'Bu)=255.17

Intermediate V: (2S,3R)-1-methyl-2-(2-naphthylmethyl)pyrrolidin-3-amine

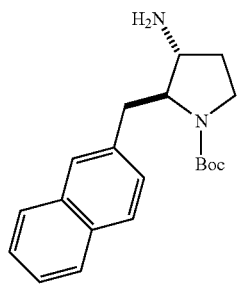

This compound was prepared in a similar manner to intermediate I but substituting (S)-N-Boc-2-naphthylalanine in place of Boc-L-Phe as the reactant. ¹H NMR (CDCl₃) δ 8.46 (bs, 2H), 7.79 (m, 3H), 7.58 (s, 1H), 7.45 (m, 2H), 7.30 (m, 1H), 4.32-4.22 (m, 1H), 3.58 (m, 2H), 3.31 (m, 1H), 3.17 (m, 1H), 2.88 (m, 1H), 1.96 (m, 2H), 1.47 (s, 9H). LCMS (M−Boc)=227.26

Intermediate VI: (2S,3R)-2-cyclopropylmethyl-1-methylpyrrolidin-3-amine

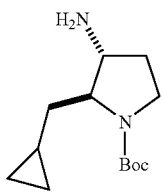

This compound was prepared in a similar manner to intermediate I but substituting (S)-N-Boc-cyclopropylalanine in place of Boc-L-Phe as the reactant. LCMS (M−Boc)=141.18

Intermediate VII: (2S,3R)-2-(3-fluorobenzyl)-1-methylpyrrolidin-3-amine

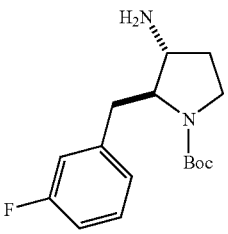

This compound was prepared in a similar manner to intermediate I but substituting (S)-N-Boc-3-fluorophenylalanine in place of Boc-L-Phe as the reactant. LCMS (M−Boc)= 195.17

Intermediate VIII: (2S,3R)-1-methyl-2-(3-thienylmethyl)pyrrolidin-3-amine

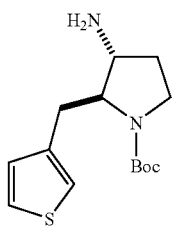

This compound was prepared in a similar manner to intermediate I but substituting (S)-N-Boc-2-thienylalanine in place of Boc-L-Phe as the reactant. LCMS (M−Boc)=183.14

Intermediate IX: (Route B) tert-butyl (2S,3R)-3-amino-2-benzyl-5-methylpyrrolidine-1-carboxylate

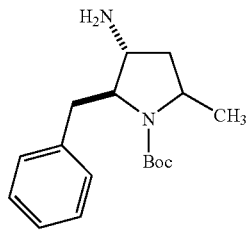

Step A: The β-hydroxylactam from intermediate I; step C (1.1 g, 3.8 mmol) was dissolved in 20 mL of DCM and 0.44 mL (3.8 mmol) of 2,6-lutidine and cooled to −70° C. TBSOTf (0.87 mL, 3.8 mmol) was introduced by syringe and the resulting reaction mixture was stirred for 3 h. The reaction was quenched by the addition of 5 mL of saturated NaHCO₃ and the two phases were separated. The organic phase was washed with 5 mL water, 5 mL of 5% citric acid, and 5 mL of brine. Column chromatography (1:4 EtOAc/Hexanes) of the stripped down organic extract afforded the silyl ether. ¹H NMR (CDCl₃) δ 7.21-7.11 (m, 5H), 4.44-4.31 (m, 2H), 3.11 (dd, 1H), 2.88 (dd, 1H), 2.38 (dd, 1H), 2.18 (dd, 1H), 1.38 (s, 9H), 0.88 (s, 9H), 0.03 (s, 6H). LCMS (M−Boc)=306.31

Step B: A solution containing 1.5 g (4.0 mmol) of the lactam from step A in 20 mL of THF at −70° C. was treated with 1.7 mL (5.2 mmol) of 3M MeMgI in ether. The reaction was stirred to rt over 2 h, quenched with saturated NH$_4$Cl and extracted with ether. The organic extracts were dried over MgSO$_4$ and the solvents were removed to afford the crude animal. This material was dissolved in EtOH (30 mL), cooled to 0° C. and treated with 175 mg (4.74 mmol) of NaBH$_4$. The reaction was stirred to rt over 8 h before the ethanol was removed under reduced pressure. The residue was covered with 25 mL of EtOAc and quenched with saturated NH$_4$Cl. The organic phase was separated and chromatographed (1:1 EtOAc/Hexanes) to afford the methyl carbinol as a mixture of diastereomers. $^1$H NMR (CDCl$_3$) δ 7.41-7.08 (m, 5H), 4.65 (m, 1H), 4.03 (m, 1H), 3.83 (m, 1H), 2.88 (m, 1H), 2.71 (m, 1H), 1.66 (m, 2H), 1.21 (d, 3H), 0.088 (s, 9H), 0.80 (s, 6H), 0.03 (s, 6H). LCMS (M−Boc)=324.36

Step C: A 0° C. solution of the alcohol from step B (650 mg, 1.54 mmol) in 10 mL of DCM was treated with 0.214 mL (1.54 mmol) of TEA and 0.118 mL (1.54 mmol) of methanesulfonyl chloride. The reaction mixture was stirred for 2 h, diluted with 100 mL of DCM then washed with saturated NaHCO$_3$ (3×20 mL), water (25 mL) and brine (25 mL). The organic phase was dried over MgSO$_4$ and concentrated to leave the desired mesylate as an oil that was used in the next reaction without further purification. LCMS (M−Boc)= 402.29

Step D: A solution containing 753 mg (1.5 mmol) of the mesylate from step C in 10 mL of THF was cooled to 0° C. and treated with 1.5° mL (1.5 mmol) of 1M KO$^t$Bu in THF. The reaction was stirred to rt over 16 h, quenched with saturated NH$_4$Cl and diluted with 25 mL of ether. The organic phased was washed with brine and dried over MgSO$_4$. Column chromatography (2:3 EtOAc/Hexanes) left the desired pyrrolidine. LCMS (M−$^t$Bu)=350.32

Step E: The silyl ether from step D (260 mg, 0.642 mmol) was dissolved in 5 mL of THF, cooled to −70° C. and treated with 0.70 mL (0.70 mmol) of 1M TBAF in THF. The reaction mixture was allowed to come to rt slowly over 3 h. The solvent was evaporated and chromatographed (1:1 EtOAc/Hexanes) to afford the desired alcohol. LCMS (M−$^t$Bu)=236.23

Step F: A 0° C. solution of the alcohol from step E (78 mg, 0.27 mmol) in 2 mL of DCM was treated with 0.037 mL (0.27 mmol) of TEA and 0.021 mL (0.27 mmol) of methanesulfonyl chloride. The reaction mixture was stirred for 1 h, diluted with 15 mL of DCM then washed with saturated NaHCO$_3$ (3×3 mL), water (3 mL) and brine (3 mL). The organic phase was dried over MgSO$_4$ and concentrated to leave the desired mesylate as an oil that was used in the next reaction without further purification. LCMS (M−$^t$Bu)=314.22

Step G: solution containing 100 mg (0.27 mmol) of the mesylate from step F in 1 mL of DMF was treated with 176 mg (2.7 mmol) of sodium azide and the whole was heated at 70° C. for 18 h. The reaction mixture was cooled and diluted with 15 mL of ether and washed with water (7×3 mL) and brine (5 mL). The organic phase was dried over MgSO$_4$ and concentrated to leave the desired azide that was used in the next reaction without further purification. LCMS (M−Boc)= 218.21

Step H: A solution containing 70 mg (0.22 mmol) of the azide from step 7-G in 5 mL of THF and 0.02 mL of water was treated with 98 mg (0.37 mmol) of PPh$_3$ and stirred over 17 h at 50° C. The reaction mixture was cooled and chromatographed (9:1 EtOAc/CH$_3$OH) to afford the desired amine. $^1$H NMR (CDCl$_3$) δ 7.35-7.11 (m, 5H), 4.05 (m, 1H), 3.65 (m, 1H), 3.33 (m, 1H), 3.09 (m, 1H), 2.65 (m, 1H), 1.78 (m, 2H), 1.61 (s, 3H), 1.36 (s, 9H). LCMS (M−$^t$Bu)=235.25

Intermediate X: (2S,3R)-5-allyl-2-benzyl-1-methylpyrrolidin-3-amine

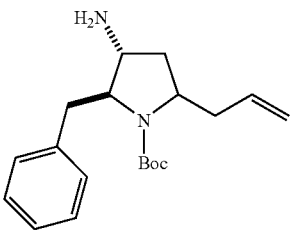

This intermediate was prepared in a manner similar to intermediate IX but substituting allyl magnesium bromide as the nucleophile in step B. LCMS (M−tBu)=261.22

EXAMPLE 1

N-[(2S,3R)-2-benzylpyrrolidin-3-yl]-N'-[(1R)-1-(4-fluorophenyl)ethyl]-5-[methyl(methylsulfonyl)amino]isophthalamide

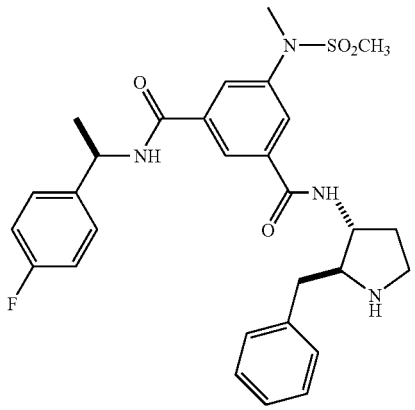

Step A: To a stirred slurry of dimethyl 5-aminoisophthalate (5.0 g, 23.9 mmol) in 100 mL CH$_2$Cl$_2$/pyridine (3:1) at 0 C was added methanesulfonyl chloride (1.85 mL, 23.9 mmol). The resulting mixture was stirred for 4 h at rt. The reaction mixture was washed with 1N HCl×3, water then brine. The solution was dried over MgSO$_4$ and evaporated to leave the desired sulfonamide as a white solid. $^1$H NMR (DMSO$_{d6}$) δ 8.15 (s, 1H), 8.02 (s, 2H), 3.89 (s, 6H), 3.02 (s, 3H) LCMS [M−OCH$_3$]$^+$=256.16.

Step B: To a solution of sodium hydride (0.153 g, 3.83 mmol, 60% oil dispersion) in 10 mL DMF was added sulfonamide (1.0 g, 3.48 mmol) from step A followed by methyl iodide (0.43 mL, 6.97 mmol). After 1 hr the reaction was quenched with H$_2$O (100 mL) and extracted with EtOAc (3×50 mL). The organic extracts were dried over MgSO$_4$ and evaporated to give the product. $^1$H NMR (DMSO$_{d6}$) δ 8.40 (s, 1H), 8.19 (s, 2H), 3.91 (s, 6H), 3.34 (s, 3H), 3.01 (s, 3H). LCMS [M+H]=302.15.

Step C: Diester (1.03 g, 3.38 mmol) from step B was dissolved in 50 mL THF:MeOH (1:1) and cooled to 0° C. 1N NaOH (3.38 mL, 3.38 mmol) was added and the reaction was allowed to warm to rt over 8 hours. The solution was acidified with 1N HCl (30 mL) and extracted with EtOAc (3×50 mL). The combined organic extracts were washed with brine and dried over MgSO4, filtered and concentrated in vacuo. Purification on silica gel (5% MeOH/CHCl3 containing 1%

HOAc) gave the mono acid. 1H NMR (DMSO $_{d6}$) δ 8.30 (s, 1H), 8.10 (s, 2H), 3.84 (s, 3H), 3.27 (s, 3H), 2.94 (s, 3H). LCMS (M+H)=288.16.

Step D: A solution containing 133 mg (0.46 mmol) of the monoacid from step C in 5 mL DCM, BOP reagent (235 mg, 0.55 mmol), (R)-(+)-4-fluoro-α-methylbenzylamine (0.55 mmol), and diisopropylamine (0.24 mL, 1.39 mmol) was stirred at ambient temperature for 1 h. Evaporation of the solvent and column chromatography on silica gel (90% EtOAc/Hexanes) afforded the desired benzyl amide. $^1$H NMR (CDCl$_3$) δ 8.26 (s, 1H), 8.17 (s, 1H), 8.06 (s, 1H), 7.31 (m, 4H), 6.50 (d, J=7.1 H, 1H), 5.33 (q, J=7.1 Hz, 1H), 3.96 (s, 3H), 3.37 (s, 3H), 2.88 (s, 3H), 1.64 (d, J=7.0 Hz, 3H). LCMS (M+H)=409.20.

Step E: To 179 mg (0.438 mmol) of the benzyl amide from step D in 10 mL THF:MeOH (1:1) was added 2 N NaOH (0.66 mL, 1.32 mmol). The solution was heated to 50° C. for 1 h. After cooling the solution was acidified by the addition of 1 N HCl (20 mL) and extracted with EtOAc (3×30 mL). The combined organic extractions were dried over MgSO$_4$, filtered, and concentrated in vacuo to yield the desired carboxylic acid. $^1$H NMR (CDCl$_3$) d 8.22 (t, 1H), 8.11 (m, 1H), 8.06 (m, 1H), 7.34 (m, 4H), 6.47 (d, J=7.1 Hz, 1H), 5.33 (m, 1H), 3.37 (s, 31H), 2.87 (s, 3H), 1.64 (d, J=7.0 Hz, 3H). LCMS (M+H)=395.2.

Step F: A solution containing 59.1 mg (0.15 mmol) of the carboxylic acid from step 1-E, 41 mg (0.15 mmol) of intermediate pyrrolidine I, 67.2 mg (0.15 mmol) of BOP reagent and 0.079 mL (0.46 mmol) of Hunig's base was stirred at rt for 1 h in 1 mL of DCM. The solvent was evaporated and the residue was purified by reverse phase chromatography to afford the Boc protected pyrrolidine. LCMS (M–Boc)=553.21.

Step G: This material was dissolved in 1 mL of DCM and treated with 1 mL of TFA. The solution was stirred at rt for 30 min before the solvent was evaporated and purified by reverse phase chromatography. $^1$H NMR (CD$_3$OD) δ 8.91 (d, J=7.6 Hz, 1H), 8.05 (s, 1H), 8.01 (s, 1H), 7.88 (s, 1H), 7.43 (m, 2H), 7.30 (m, 3H), 7.20 (m, 1H), 7.07 (t, J=8.7 Hz, 1H), 5.24 (t, J=6.9 Hz, 1H), 4.53 (q, J=7.8 Hz, 1H), 3.87 (q, J=7.8 Hz, 1H), 3.46 (t, J=7.3 Hz, 2H), 3.35 (s, 3H), 3.25 (dd, J=14.3, 8.6 Hz, 1H), 3.03 (dd, J=14.3, 8.6 Hz, 1H), 2.97 (s, 3H), 2.44 (m, 1H), 2.11 (m, 1H), 1.55 (d, J=7.0 Hz, 3H). LCMS (M+H)=553.18

EXAMPLE 2

N-[(2S,3R)-2-(3-chlorobenzyl)pyrrolidin-3-yl]-3-{[(2-methylcyclopropyl)oxy]methyl}-5-[methyl(methylsulfonyl)amino]benzamide

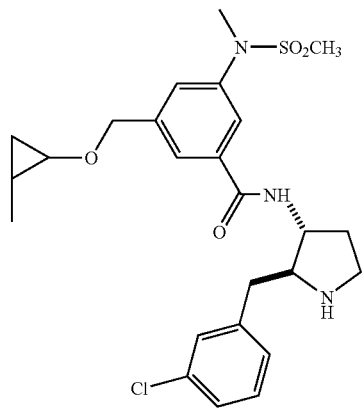

Step A: To a stirred solution of dimethyl 5-hydroxyisophthalate (8.6 g, 41.1 mmol) in 200 mL of acetone was added K$_2$CO$_3$ (5.7 g, 41.1 mmol) and trans-crotyl bromide (5.5 g, 41.1 mmol). The resulting mixture was stirred at reflux for 16 h. The solids were removed by filtration and the filtrate was evaporated to near dryness. The resulting residue was dissolved in 200 mL of ether and washed 3×20 mL of 1N HCl then brine. The organic extracts were dried over MgSO$_4$ and evaporated to give aryl ether A. $^1$H NMR (CDCl$_3$) δ 8.25 (s, 1H), 7.75 (s, 2H), 5.93 (m, 1H), 5.77 (m, 1H), 4.58 (d, J=2.2 Hz, 2H), 3.91 (s, 6H), 1.81 (d, J=2.2 Hz, 3H). LCMS (M+H)=265.24.

Step B: A 0° C. solution containing 9.4 g (35.6 mmol) of the isophthalate from step A in 300 mL of a 1:1 mixture of THF and MeOH was treated with 35.6 mL (35.6 mmol) of 1N NaOH. The ice bath was allowed to stir to ambient temperature over 16 h. The reaction mixture was concentrated to ca. 1/8 volume before it was acidified with 25 mL of 3N HCl. The solids that precipitated were redissolved in 300 mL of EtOAc and washed with brine (2×25 mL). The organic extract was dried over MgSO$_4$ and evaporated to afford the desired carboxylic acid. $^1$H NMR (CDCl3) δ 8.37 (s, 1H), 7.82 (s, 2H), 5.93 (m, 1H), 5.77 (m, 1H), 4.58 (d, J=2.2 Hz, 2H), 3.95 (s, 3H), 1.77 (d, J=2.2 Hz, 3H). LCMS (M+H)=252.18

Step C: To a 0° C. solution containing 4.0 g (16.0 mmol) of carboxylic acid II-C in 80 mL of THF was added 4.2 mL (30.2 mmol) of Et$_3$N and 2.2 mL (22.7 mmol) of ethyl chloroformate. The resulting slurry was stirred for 1 h and treated with 2.46 g (37.8 mmol) of NaN$_3$ dissolved in 15 mL of water. After an additional hour at rt the reaction mixture was diluted with 50 mL of water and washed toluene (3×50 mL). The combined organic extracts were dried over MgSO$_4$ and refluxed over 16 h. The reaction was cooled to rt and treated with 3.1 mL (30.2 mmol) of benzyl alcohol and 4.2 mL (30.2 mL) of triethylamine. The reaction was refluxed for 24 h, cooled and diluted with 100 mL of EtOAc and 35 mL of 10% citric acid. The organic extract was washed with water and brine then dried over MgSO$_4$. Column chromatography (2:3 EtOAc/Hexanes) afforded the arylether C. $^1$H NMR (CDCl$_3$) δ 7.38 (m, 8H), 6.85 (bs, 1H), 5.85 (m, 1H), 5.65 (m, 1H), 5.20 (s, 2H), 4.44 (d, J=6.0 Hz, 2H), 3.82 (s, 3H), 1.71 (d, 3H). LCMS (M+H)=356.25

Step D: A solution of 3.56 g (10.0 mmol) of the aryl ether from step C was dissolved in 100 mL of EtOAc and treated with 50 mL (c.a. 0.5 M, 25 mmol) of freshly prepared CH$_2$N$_2$. After stirring for 5 min, 112 mg (0.5 mmol) of Pd(OAc)$_2$ was added to effect vigorous release of N$_2$. After an additional 30 min, the brown slurry was evaporated and chromatographed (1:1 EtOAc/Hexanes) to afford the cyclopropylmethyl ether D. $^1$H NMR (CDCl$_3$) δ 7.55 (s, 1H), 7.44 (m, 7H), 6.80 (bs, 1H), 5.23 (s, 2H), 3.85 (s, 3H), 3.80 (m, 2H), 1.04 (d, 3H), 0.94 (m, 1H), 0.75 (m, 1H), 0.47 (m, 1H), 0.38 (m, 1H). LCMS (M+H)=368.26

Step E: A solution of the benzyl carbamate (3.6 g, 10.0 mmol) from step D and 1.5 g of 10% Pd/C in EtOAc (100 mL) was stirred at rt under a balloon of hydrogen gas for 5 h. The mixture was filtered through a pad of Celite, concentrated, and purified on silica gel (50% EtOAc/Hexanes) to afford the desired aniline. $^1$H NMR (CDCl$_3$) δ 6.99 (s, 2H), 6.40 (s, 1H), 3.85 (s, 3H), 3.75 (m, 2H), 1.77 (m, 1H), 1.45 (m, 1H), 1.04 (d, 3H), 0.47 (m, 1H), 0.33 (m, 1H). LCMS (M+H)=236.2.

Step F: To a 0° C. solution of the aniline from step E (940 mg, 4.0 mmol) in 30 mL of DCM and 5 mL of pyridine was added methanesulfonyl chloride (0.40 mL, 4.0 mmol). The resulting mixture was stirred at this temperature for 2 h before being diluted with 100 mL of DCM. The solution was washed with 1N HCl (3×25 mL), water (2×25 mL), and brine (25 mL). The organic phase was dried and concentrated to afford sulfonamide P which was used in the next step without further purification. LCMS (M+H)=314.1

Step G: The sulfonamide from step F (1.25 g, 4.0 mmol) in DMF (20 mL) was treated with 95% sodium hydride (106 mg, 4.4 mmol) and excess methyl iodide (3 mL). The resulting mixture was stirred at ambient temperature for 1 h and was diluted with 200 mL of ether. The solution was washed with water (7×25 mL) and brine then dried over MgSO$_4$. Purification by silica gel chromatography (2:3 EtOAc/Hexanes) afforded the desired methylated sulfonamide. $^1$H NMR (CDCl$_3$ w/0.05% DMSO-$_{d6}$) δ 7.65 (s, 1H), 7.41 (s, 1H), 7.15 (s, 1H), 3.93 (s, 3H), 3.80 (t, 2H), 3.30 (S, 3H), 2.87 (s, 3H), 1.11 (d, 3H), 0.88 (m, 1H), 0.55 (m, 1H), 0.37 (m, 1H). LCMS (M+H)=328.23

Step H: To a stirred solution of the ester from step G (625 mg, 2.0 mmol) in 12 mL THF/MeOH (1:1) was added 15% NaOH (2.2 mL, 8.0 mmol). After the reaction mixture was stirred at 45° C. for 2 h the solvents were evaporated and the residue was acidified with 3N HCl (4.0 mL, 121 mmol). The solid was taken up in 75 mL of DCM and the organic phase was washed with brine. The organic phase was dried and evaporated to yield the desired carboxylic acid as a white solid. $^1$H NMR (CDCl$_3$ w/0.05% DMSO-$_{d6}$) δ 7.61 (s, 1H), 7.44 (s, 1H), 7.15 (s, 1H), 3.83 (t, 2H), 3.32 (S, 3H), 2.83 (s, 3H), 1.11 (d, 3H), 0.88 (m, 1H), 0.55 (m, 1H), 0.37 (m, 1H). LCMS (M+H)=314.22

Step I: A solution containing 47 mg (0.15 mmol) of the carboxylic acid from step H, 47 mg (0.15 mmol) of intermediate pyrrolidine III, 67.2 mg (0.15 mmol) of BOP reagent and 0.079 mL (0.46 mmol) of Hunig's base was stirred at rt for 1 h in 1 mL of DCM. The solvent was evaporated and the residue was purified by reverse phase chromatography to afford the Boc protected pyrrolidine. LCMS (M−Boc)= 407.06.

Step J: The material from example 2-I was dissolved in 1 mL of DCM and treated with 1 mL of TFA. The solution was stirred at rt for 30 min before the solvent was evaporated and purified by reverse phase chromatography. $^1$H NMR (CD$_3$OD) δ 7.4-7.15 (m, 7H), 4.55 (q, J=8.1 Hz, 1H), 3.87 (q, J=7.8 Hz, 1H), 3.83 (m, 1H), 3.46 (t, J=7.3 Hz, 2H), 3.31 (s, 3H), 3.22-3.11 (m, 2H), 3.03 (dd, J=14.3, 8.6 Hz, 1H), 2.97 (s, 3H), 2.54 (m, 1H), 2.19 (m, 1H), 1.05 (d, J=7.0 Hz, 3H), 0.97 (m, 1H), 0.81 (m, 1H), 0.57 (m, 1H), 0.38 (m, 1H). LCMS (M+H)=506.24

EXAMPLE 3

N-[(2S,3R)-2-benzylpyrrolidin-3-yl]-3-[methyl(methylsulfonyl)amino]-5-[(2-phenylcyclopropyl)methoxy]benzamide

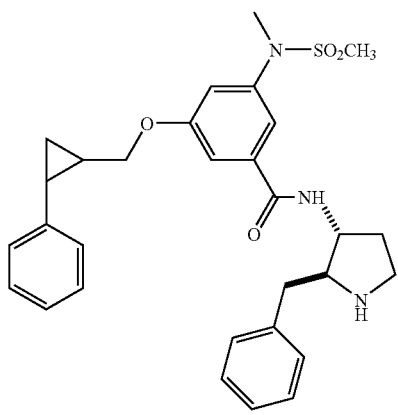

This compound was prepared in a manner analogous to Example 2. $^1$H NMR (CD$_3$OD) δ 8.59 (bs, 1H), 7.4-7.1 (m, 13H), 4.21 (m, 1H), 4.02 (m, 1H), 3.87 (q, J=7.8 Hz, 1H), 3.46 (t, J=7.3 Hz, 2H), 3.30 (s, 3H), 3.25 (dd, J=14.3, 8.6 Hz, 1H), 3.03 (dd, J=14.3, 8.6 Hz, 1H), 2.92 (s, 3H), 2.51 (m, 1H), 2.14 (m, 1H), 2.03 (m, 1H), 1.63 (m, 1H), 1.08 (t, J=7.0 Hz, 2H). LCMS (M+H)=534.27

EXAMPLE 4

N-[(2S,3R)-2-benzylpyrrolidin-3-yl]-3-[(cyclopropyloxy)methyl]-5-[methyl(methylsulfonyl)amino]benzamide

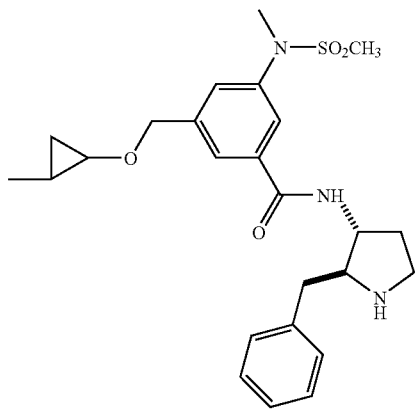

This compound was prepared in a manner similar to Example 2 employing intermediate carboxylic acid 2-H and pyrrolidine intermediate I. LCMS (M+H)=486.23

EXAMPLE 5

N-[(2S,3R)-2-(3-chlorobenzyl)pyrrolidin-3-yl]-3-{(Z)-2-[(1S,2S)-2-methylcyclopropyl]vinyl}-5-[methyl(methylsulfonyl)amino]benzamide

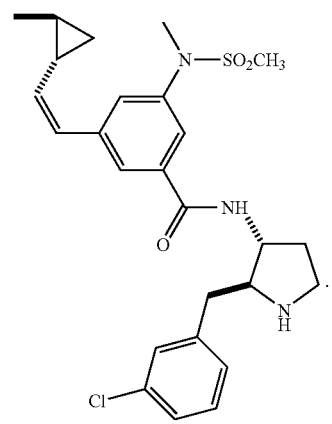

Step A: 3-Nitrobenzoate (35.3 g, 195 mmol) in triflic acid (100 mL) at 0° C. was added NIS (43.8 g, 195 mmol) in ten portions. The ice bath was removed and the solution stirred for 48 hrs. At this time, more NIS was added to cool to 0° C. and the solution was quenched with dropwise addition of water. The mixture was extracted three times with EtOAc (250 mL) and the combined extracts were washed with a 10% NaHSO$_3$ solution, followed by water. The organics were dried over Na$_2$SO$_4$, concentrated, and purified on silica gel (10% EtOAc in Hex) affording 24.1 g.

Step B: Tin chloride (88.6 g, 392 mmol) in EtOH (50 mL) was refluxed and the nitrobenzoate from step A (24.1 g, 78.4 mmol) in 1:1 ThF:EtOH (100 mL) was added dropwise. The reaction mixture was refluxed for 30 min then cooled to 0° C. The resulting solution was basified to pH 8-9 with aq. Na$_2$CO$_3$. The aqueous layer was extracted three times with EtOAc (700 mL) and the combined extracts were washed with saturated NaHCO$_3$ then brine. The organics were dried over Na$_2$SO$_4$ and concentrated to afford the crude aniline which was used without further purification.

Step C: To a 0° C. solution of aniline from step B (21.7 g, 78.3 mmol) in 3:1 DCM:pyridine (75 mL) was added methanesulfonyl chloride (6.36 mL, 82.2 mmol). The ice bath was removed after 15 min and the solution was stirred overnight at rt. The reaction mixture was extracted several times with 1N HCl. The organic phase was dried, concentrated, and chromatographed (1:1 EtOAc:Hex) to afford the desired sulfonamide as a white solid.

Step D: The sulfonamide from step C (23.6 g, 66.5 mmol) in DMF (75 mL) at 0° C. was treated with 60% NaH (2.92 g, 73.1 mmol). The solution stirred for 30 min before MeI (4.55 mL, 73.1 mmol) was added. The ice bath was removed and the solution was stirred at rt for twelve hours. The reaction was quenched with saturated NH$_4$Cl solution and extracted three times with EtOAc (150 mL). The combined organics were washed with water (5×50 mL), dried, concentrated to afford the desired methylated anilide which was used without further purification.

Step E: Trans-2-methylcyclopropanemethanol (7.0 g, 81 mmol) was added to a solution of PCC (28 g, 130 mmol) in CH$_2$Cl$_2$ (225 mL). The solution became black and was stirred for three hours at rt. The reaction mixture was diluted with ether (250 mL) and decanted. The liquid solution was filtered through a 4 inch plug of Florisil and the solvent was removed by distillation through a Vigreux column to afford the desired aldehyde.

Step F: To a solution of PPh$_3$ (12.4 g, 47.5 mmol) in CH$_2$Cl$_2$ (100 mL) at 0° C. was added CBr$_4$ (7.88 g, 23.7 mmol). The reaction mixture was stirred for 10 min then treated with the carboxaldehyde from step E (1.0 g, 12 mmol). The solution was stirred for 30 min at 0° C. then 1 hr at rt. Hexane was added and the solids were filtered, and the filtrate was concentrated to afford the dibromide.

Step G: The dibromide from step F (15.4 g, 64.1 mmol) in 60 mL of cyclohexane at −78° C. was treated with 2.0 M n-BuLi in cyclohexane (64.1 mL, 128 mmol). The resulting reaction mixture was stirred at 78° C. for 1 hr then warmed to rt where it was stirred for 2 hr. The reaction was quenched with water and extract with cyclohexane (3×25 mL). The product was purified by distillation (bp=69-72° C.).

Step H: A 100 mL 3-neck round bottom flask was charged with InCl$_3$ (0.829 g, 10.4 mmol) and dried under vacuum with a heat gun for 2 min. THF (16 mL) was added under nitrogen and the flask was immersed in a −78° C. ice bath. DIBAL-H (12.4 mL, 1M in hexanes) was then added dropwise and the resulting solution was stirred for 30 min at −78° C. After this time, the acetylene from step G (10.4 mmol) was added followed by 1.0 M Et$_3$B (1.6 mL, 1M in hexanes). This reaction mixture was stirred at −78° C. for 2.5 hr then warmed to rt. DMI (12 mL) and aryliodide from step D (1.47 g, 4.0 mmol) was added followed by a palladium trifurylphosphine complex [prepared from Pd$_2$(DBA)$_3$CHCl$_3$ (20 mg) and trifurylphosphine (28 mg) in THF (6 mL)]. The resulting reaction mixture was heated at 60° C. for 2 hr, quenched with water and extracted with ether (3×50 mL). The combined organic extracts were dried, and concentrated and the product was purified on a chiral OJ column (6:4 Hexane w/0.1% TFA:EtOH). Collection of the first peak afforded the desired diastereomer.

Step I: To 276 mg (0.853 mmol) of the ester from step H in 10 mL THF:MeOH:water (3:1:1) was added 2 N NaOH (0.64 mL, 1.28 mmol). The solution was stirred at rt for 2 h. The reaction mixture was concentrated and acidified with 2 N HCl (10 mL) and extracted with CHCl$_3$ (3×20 mL). The combined organic extracts were dried over MgSO$_4$, filtered, and concentrated to yield the desired carboxylic acid. LCMS (M+H)= 310.12

Step J: A solution containing 8.0 mg (0.026 mmol) of the carboxylic acid from step I, 10.6 mg (0.031 mmol) of intermediate pyrrolidine III, 8.06 mg (0.026 mmol) of BOP reagent and 0.026 mL (0.11 mmol) of Hunig's base was stirred at rt for 1 h in 3 mL of DCM. The solvent was evaporated and the residue was purified by reverse phase chromatography to afford the Boc protected pyrrolidine. This material was dissolved in 2 mL of DCM and treated with 0.5 mL of TFA. The solution was stirred at rt for 30 min before the solvent was evaporated and purified by reverse phase chromatography. $^1$H NMR (400 MHz, CDCl$_3$) δ 8.25 (bs, 1H), 7.82 (s, 1H), 7.65 (m, 2H), 7.41-7.15 (m, 4H), 6.25 (d, 1H), 5.20 (t, 1H), 4.76 (m, 1H), 4.05 (m, 1H), 3.55 (m, 1H), 3.33 (s, 3H), 3.18 (m, 1H), 2.81 (s, 3H), 2.44 (m, 1H), 2.25 (m, 1H), 1.04 (d, 3H), 0.86 (m, 1H), 0.61 (m, 1H). LCMS (M+H)= 501.98

EXAMPLE 6

N-butyl-N'-[(2S,3R)-2-(3-chlorobenzyl)pyrrolidin-3-yl]-2'-cyano-N-methylbiphenyl-3,5-dicarboxamide

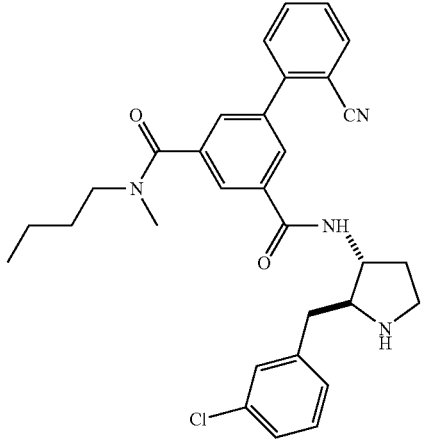

BOP mediated coupling between intermediate pyrrolidine III and 5-{[butyl(methyl)amino]carbonyl}-2'cyanobiphenyl-3-carboxylic acid followed by Boc deprotection afforded the desired compound. $^1$H NMR (400 MHz, CDCl$_3$) δ 10.6 (bs, 1H), 8.71 (bs, 1H), 8.52 (bt, 1H), 8.03 (s, 1H), 7.94 (s, 1H), 7.76 (d, J=7.7 Hz, 1H), 7.67 (m, 3H), 7.59 (m, 1H), 7.59 (m, 1H), 7.3-7.11 (m, 3H), 4.65 (m, 1H), 4.08 (m, 1H), 3.51 (t, J=7.6 Hz, 1H), 3.4-3.2 (m, 3H), 2.99 (m, 1H), 2.41 (m, 1H), 2.17 (m, 1H), 1.61 (m, 1H), 1.55 (m, 1H), 1.41 (m, 1H), 1.07 (m, 1H), 0.96 (t, J=7.2 Hz, 3H), 0.78 (t, J=7.3 Hz, 3H). HRMS (ES)=529.2344.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:
1. A compound of formula (I):

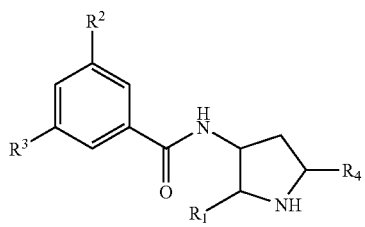

wherein:
R$^1$ is
—(CH$_2$)$_x$—Q$^1$;
R$^2$ is selected from the group consisting of:
(1) (R$^5$—SO$_2$)N(R$^7$)—,
(2) R$^5$—S(O)$_m$—,
(3) R$^5$NHC(=O)—,
(4) R$^5$C(=O)NH—,
(5) R$^5$R$^{5'}$N—,
(6) CN,
(7) —C$_{1-6}$alkyl,
(8) halogen, and
(9)

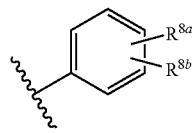

R$^3$ is selected from the group consisting of:

(1) 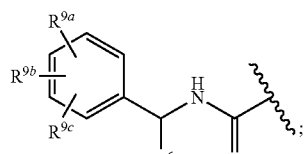

(2) 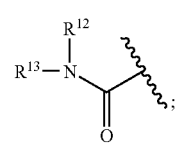

(3) 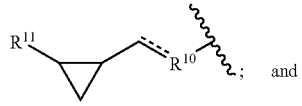  and (4) 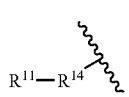

R$^4$ is selected from the group consisting of:
(1) hydrogen, and
(2) —C$_{1-6}$alkyl;
R$^5$, R$^{5'}$ and R$^6$ are each independently selected from the group consisting of:
(1) —C$_{1-6}$alkyl,
(2) —C$_{2-6}$alkenyl,
(3) —C$_{2-6}$alkynyl,
(4) —C$_{3-8}$ cycloalkyl, and
(5) —(CH$_2$)$_x$— phenyl;
R$^7$ is selected from the group as consisting of;
(1) hydrogen,
(2) —C$_{1-6}$alkyl,
(3) —C$_{2-6}$alkenyl,
(4) —C$_{2-6}$alkynyl, and
(5) —(CH$_2$)$_x$—phenyl;
R$^{8a}$ and R$^{8b}$ are independently selected from the group consisting of:
(1) —CN,
(2) hydrogen,
(3) halogen,
(4) -Q$^2$R$^5$,
(5) —C$_{1-6}$alkyl,
(6) —CO$_2$R$^5$, and
(7) tetrazolyl;
R$^{9a}$, R$^{9b}$, R$^{9c}$, R$^{9d}$ and R$^{9e}$ are each independently selected from the group consisting of:
(1) hydrogen,
(2) halogen,
(3) -Q$^2$R$^5$, and
(4) —C$_{1-6}$alkyl;
R$^{10}$ is selected from the group consisting of
(1) —HC—
(2) —O—,
(3) —S—, and
(4) —NH—,
provided that when R$^{10}$ is —CH— the dashed line forms a bond and when R$^{10}$ is —O—, —S— or —NH— the dashed line is absent;
R$^{11}$ is selected from the same group as R$^7$;
R$^{12}$ and R$^{13}$ are independently selected from the group consisting of:
(1) —C$_{1-6}$ alkyl;
(2) —C$_{2-6}$ alkyl;
(3) —C$_{2-6}$ alkynyl;
(4) —(CH$_2$)$_x$— phenyl, or
R$^{12}$ and R$^{13}$ are linked together with the nitrogen atom to which they are attached, to form the group

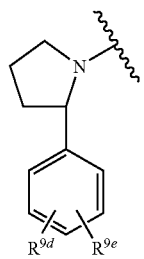

R$^{14}$ is selected from the group consisting of:
(1) —HC=CH—,
(2) —O—,
(3) —S—, and
(4) —NH—:
Q$^1$ is phenyl;

$Q^2$ is selected from the group consisting of —O— or —S—;

wherein each $R^1$, $R^2$, $R^5$, $R^{5'}$, $R^6$, $R^7$, $R^{8a}$, $R^{8b}$, $R^{9a-9e}$, $R^{11}$, $R^{12}$ and $R^{13}$ alkyl, alkenyl and alkynyl moiety herein is unsubstituted or substituted with one or more
(a) halo,
(b) —OH,
(c) —CN,
(d) —$C_{1-10}$ alkyl
(e) —$C_{3-8}$ cycloalkyl,
(f) —O—$C_{1-10}$ alkyl,
(g) aryl selected from the group consisting of phenyl or naphthyl,
(h) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl, or
(i) —$NR^7R^{11}$;
and each $R^5$, $R^{5'}$, $R^6$, $R^7$, $R^{11}$, $R^{12}$, $R^{13}$ and $Q^1$ phenyl or naphthyl moiety herein is unsubstituted or substituted with one or more
(a) halo,
(b) —OH,
(c) —CN,
(d) —$C_{1-10}$ alkyl
(e) —$C_{3-8}$ cycloalkyl,
(f) —O—$C_{1-10}$ alkyl,
(g) aryl selected from the group consisting of phenyl or naphthyl,
(h) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl, or
(i) —$NR^7R^{11}$;

m is independently 0, 1, or 2;
x is independently 0 or 1;
or a pharmaceutically acceptable salt thereof, or an individual enantiomer or diastereomer thereof.

2. The compound of claim 1 wherein $R^1$ is —($CH_2$)-phenyl.

3. The compound of claim 1 wherein $R^4$ is hydrogen or $C_{1-6}$ alkyl.

4. The compound of claim 3 wherein $R^4$ is hydrogen.

5. The compound of claim 1 wherein $R^2$ is ($R^5$—$SO_2$)N($R^7$)—.

6. The compound of claim 5 wherein $R^5$ and $R^7$ are $C_{1-6}$ alkyl.

7. The compound of claim 1 wherein $R^2$ is

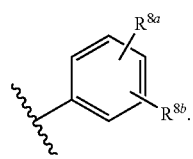

8. The compound of claim 7 wherein $R^{8a}$ is hydrogen and $R^{8b}$ is CN.

9. The compound of claim 1 which is a compound of formula (II)

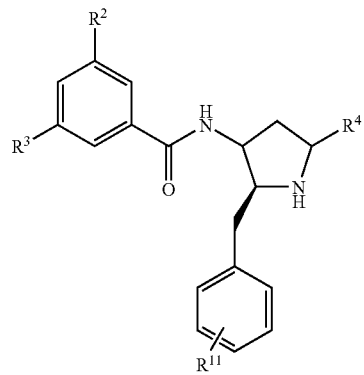

wherein $R^{11}$ is selected from the group consisting of
(1) halo,
(2) —OH,
(3) —CN, and
(4) —O—$C_{1-10}$alkyl.

10. The compound of claim 9 wherein $R^{11}$ is halogen.

11. The compound of claim 9 wherein $R^4$ is hydrogen.

12. A compound of claim 1 which is a compound of formula (III)

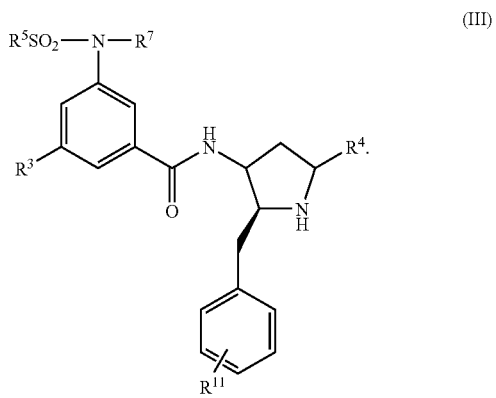

13. A compound of claim 1 which is a compound of formula (IV)

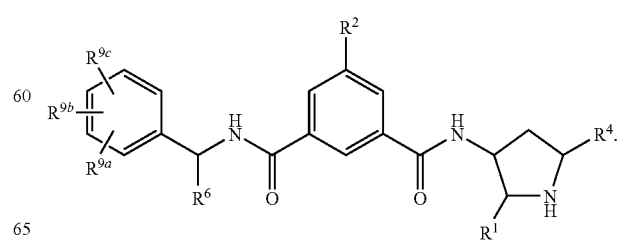

14. A compound of claim 1 which is a compound of formula (VI):

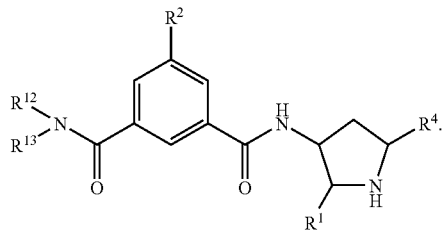

15. A compound of claim 1 which is a compound of formula (VII):

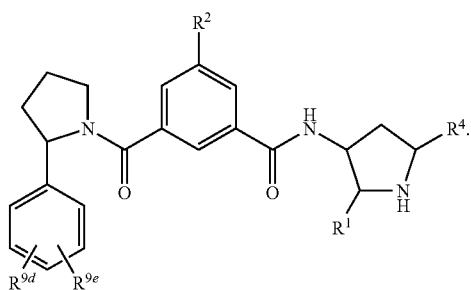

16. A compound of claim 1 which is selected from the group consisting of

N-[(2S,3R)-2-benzylpyrrolidin-3-yl]—N'-[(1R)—1-(4-fluorophenyl)ethyl]-5-[methyl(methylsulfonyl)amino]isophthalamide;

N-[(2S,3R)-2-(3-chlorobenzyl)pyrrolidin-3-yl]-3-{[(2-methylcyclopropyl)oxy]methyl}-5-[methyl(methylsulfonyl)amino]benzamide;

N-[(2S,3R)-2-benzylpyrrolidin-3-yl]-3-[methyl(methylsulfonyl)amino]-5-[(2-phenylcyclopropyl)methoxy]benzamide;

N-[(2S,3R)-2-benzylpyrrolidin-3-yl]-3-[(cyclopropyloxy)methyl]-5-[methyl(methylsulfonyl)amino]benzamide;

N-[(2S,3R)-2-(3-chlorobenzyl)pyrrolidin-3-yl]-3-{(Z)-2-[(1S,2S)-2-methylcyclopropyl]vinyl}-5-[methyl(methylsulfonyl)amino]benzamide; and N-butyl-N'-[(2S,3R)-2-(3-chlorobenzyl)pyrrolidin-3-yl]-2'-cyano-N-methylbiphenyl-3,5-dicarboxamide;

or a pharmaceutically acceptable salt thereof.

17. A pharmaceutical composition comprising a compound of claim 1 or a pharmnaceutically acceptable salt thereof and a pharmaceutically acceptable carrier.

18. A method for treating Alzheimer's disease in a patient in need thereof comprising administering to the patient a therapeutically effective amount of a compound of claim 1 or a pharmaceutically acceptable salt thereof.

* * * * *

UNITED STATES PATENT AND TRADEMARK OFFICE
CERTIFICATE OF CORRECTION

PATENT NO. : 7,714,021 B2  
APPLICATION NO. : 11/629209  
DATED : May 11, 2010  
INVENTOR(S) : Craig A. Coburn Page 1 of 1

It is certified that error appears in the above-identified patent and that said Letters Patent is hereby corrected as shown below:

Title Page, Item (73) under "Assignee", Delete "Merck & Co., Inc., Rahway, NJ (US)" and insert
-- Merck Sharp & Dohme Corp., Rahway, NJ (US) -- therefor.

Signed and Sealed this
Fourteenth Day of June, 2011

David J. Kappos
*Director of the United States Patent and Trademark Office*